United States Patent

Grubbs

Patent Number: 5,157,977
Date of Patent: Oct. 27, 1992

[54] INSPECTION MACHINE

[75] Inventor: Roy C. Grubbs, Houston, Tex.

[73] Assignee: Tuboscope Vetco International Inc., Houston, Tex.

[21] Appl. No.: 537,427

[22] Filed: Jun. 13, 1990

[51] Int. Cl.$^5$ ............... G01M 19/00; G01N 27/90
[52] U.S. Cl. ............................. 73/866.5; 73/637
[58] Field of Search ............. 73/866.5, 865.9, 865.8, 73/40.5 R, 40.5 A, 49.1, 49.5, 49.6, 622, 623, 637, 638; 324/220, 221, 242, 243

[56] References Cited

U.S. PATENT DOCUMENTS

| | | | |
|---|---|---|---|
| 3,289,468 | 12/1966 | Vander Veer et al. | 73/637 |
| 3,327,205 | 6/1967 | Wood et al. | 324/220 |
| 4,131,018 | 12/1978 | Müller et al. | 376/249 X |
| 4,152,926 | 5/1979 | Hasha | 73/49.1 X |
| 4,217,548 | 8/1980 | Furukawa et al. | 324/220 |
| 4,312,230 | 1/1982 | Bricker et al. | 73/638 |
| 4,353,257 | 10/1982 | Vrba | 73/623 |
| 4,435,006 | 3/1984 | Ishigaki et al. | 73/49.6 X |
| 4,503,393 | 3/1985 | Moyer et al. | 324/235 |
| 4,550,605 | 11/1985 | Bains | 73/622 |
| 4,567,747 | 2/1986 | Matay | 73/1 DV |
| 4,570,485 | 2/1986 | Lee, Jr. | 73/49.5 |
| 4,644,394 | 2/1987 | Reeves | 358/101 |
| 4,660,419 | 4/1987 | Derkacs et al. | 73/1 DV X |
| 4,739,273 | 4/1988 | Petersen et al. | 324/242 |
| 4,858,464 | 8/1989 | Miller et al. | 73/49.5 |

FOREIGN PATENT DOCUMENTS

| | | | |
|---|---|---|---|
| 278259 | 5/1990 | German Democratic Rep. | 73/866.5 |
| 1232318 | 5/1980 | U.S.S.R. | 73/866.5 |
| 1089502 | 4/1984 | U.S.S.R. | 73/866.5 |
| 2032046 | 4/1980 | United Kingdom | 73/866.5 |
| 2074327 | 10/1981 | United Kingdom | 73/638 |

OTHER PUBLICATIONS

Uniwest—"Eagle Plus" product brochure 4 pages; pub. by Jun. 1990.
GE Aircraft Engines—"NDE Systems and Services" product brochure pub. Oct. 1987 4 pages.
Robbin—"High Performance Eddy Current Scanner" product sheet pub. by Jun. 1990.

*Primary Examiner*—Tom Noland
*Attorney, Agent, or Firm*—Finnegan, Henderson, Farabow, Garrett & Dunner

[57] ABSTRACT

The apparatus of the present invention is a machine for feeding, indexing, testing, and storing tubular goods. The machine concentrates on the end segments of the tubular goods. The machine uses the eddy current test method to test the outer surface, the inner surface, and internal and external threads. The tests may be conducted simultaneously and at each end of the pipe. The pipe is spun during the examination so that the sensors of the inner and outer surfaces, when driven, trace a helical pattern on the pipe, and the thread sensor is driven along the thread by the rotational force applied to the pipe being tested.

11 Claims, 5 Drawing Sheets

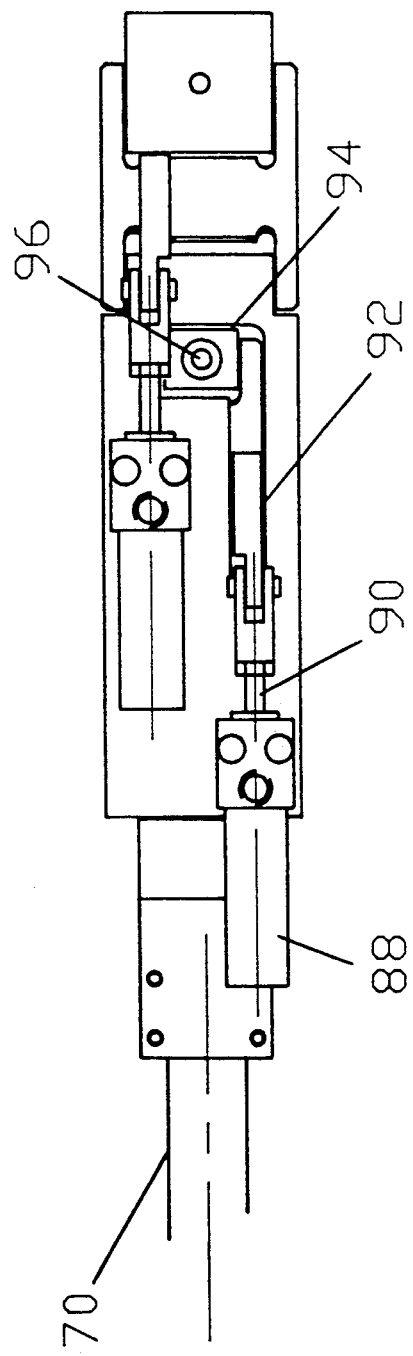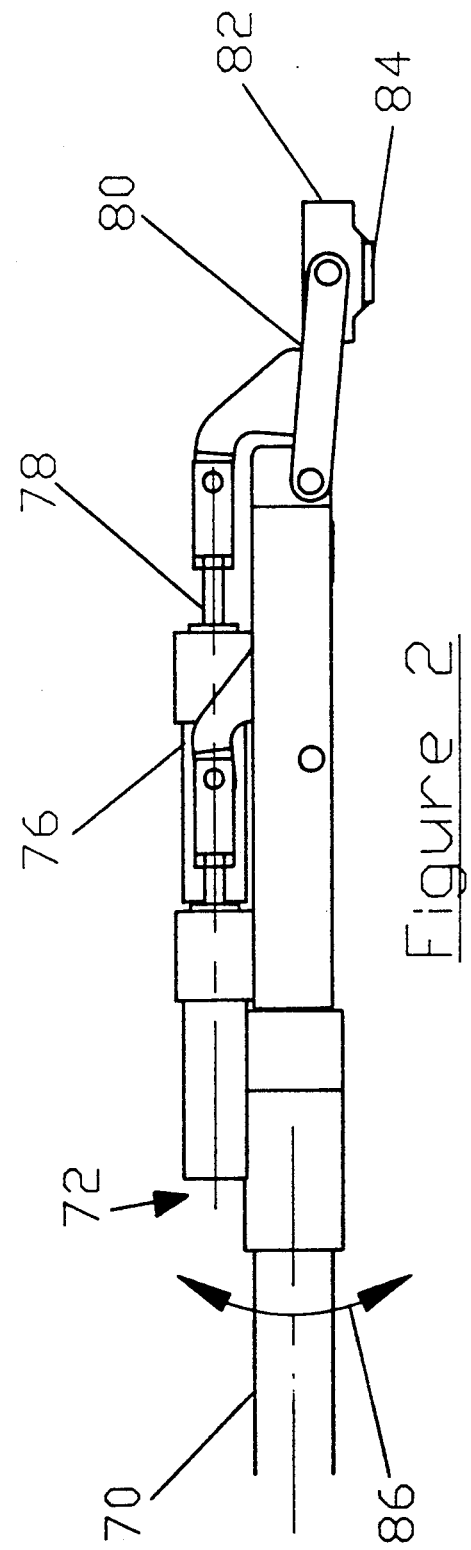

INSPECTION MACHINE

FIELD OF THE INVENTION

The field of this invention relates to the machines for testing the quality of tubular goods, particularly the end segments of tubular goods.

BACKGROUND OF THE INVENTION

Numerous types of inspection techniques have been employed to test the quality of tubular goods before they are put to use. Such types of tests have included ultrasonic inspection, eddy current inspection, and other types of inspection. One such machine for ultrasonic inspection is revealed in U.S. Pat. No. 4,567,747. This machine illustrates movement of the piece through a collar to obtain the readings on pipe quality. Yet other machines involve moving the piece through a sensor to determine its quality via ultrasonic testing. Typical of these machines are those shown in U.S. Pat. No. 4,660,419. Yet other types of machines detect flaws on the inner surface of a pipe using magnetic fields. This type of machine employs movable exciting magnets and a corresponding detector assembly to inspect the pipe. This type of machine is illustrated in U.S. Pat. No. 4,217,548.

Other machines employ eddy current techniques of non-destructive inspection. Such machines have moving probes that inspect the inner and outer surfaces of the pipe. This type of machine is illustrated in U.S. Pat. No. 4,550,605.

Machines have been developed to inspect threads at ends of pipes. These machines are illustrated in U.S. Pat. Nos. 3,327,205 and 4,503,393.

Mechanical manipulation tables for pieces to be inspected by eddy current techniques have been developed by the General Electric Company. These manipulators move a piece in three dimensions to bring it in contact with a sensor.

SUMMARY OF THE INVENTION

The apparatus of the present invention is a machine for feeding, indexing, testing, and storing tubular goods. The machine concentrates on the end segments of the tubular goods. The machine uses the eddy current test method to test the outer surface, the inner surface, and internal and external threads. The tests may be conducted simultaneously and at each end of the pipe. The pipe is spun during the examination so that the sensors of the inner and outer surfaces, when driven, trace a helical pattern on the pipe, and the thread sensor is driven along the thread by the rotational force applied to the pipe being tested.

BRIEF DESCRIPTION OF THE DRAWINGS

FIG. 2 is an elevational view of the inner surface sensor support assembly.

FIG. 3 is a plan view looking down on the inner surface sensor support assembly.

DETAILED DESCRIPTION OF THE PREFERRED EMBODIMENT

Figure 1:
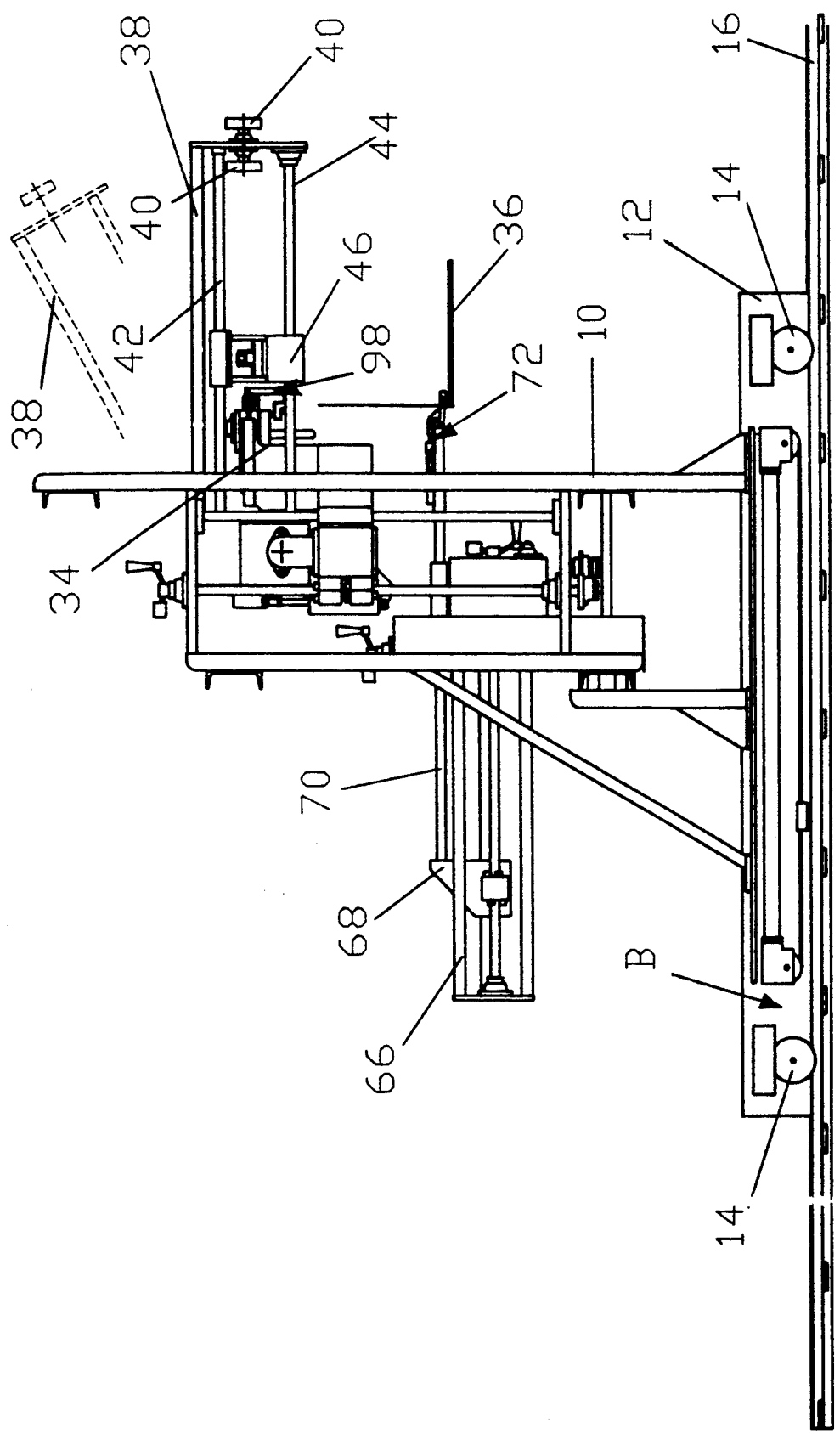
FIG. 1 is an elevational view of the machine placed at one end of a pipe to be tested. A counterpart can be used at the other end of the pipe to be tested.

The apparatus A is shown in FIG. 1. It consists of a frame 10 which extends vertically from a base 12. Base 12 is mounted on rollers 14, which are in turn operable on track 16. Base 12 can be positioned in a variety of locations on track 16 through operation of base positioning means B. As shown in FIG. 1, base positioning means B involves a piston mounted to a cylinder connected to a cable which is connected to pulleys which, when actuated, can move base 12 selectively in two directions. Those skilled in the art will appreciate that various positioning means can be employed to locate base 12 in the desired position. Outer surface carriage support subframe 38 and datum roll 34 can be vertically adjusted, depending on the outer diameter of the pipe to be tested. Support subframe 66 also can be independently vertically adjusted, depending on the outer diameter and wall thickness of the pipe to be tested.

Figure 4:
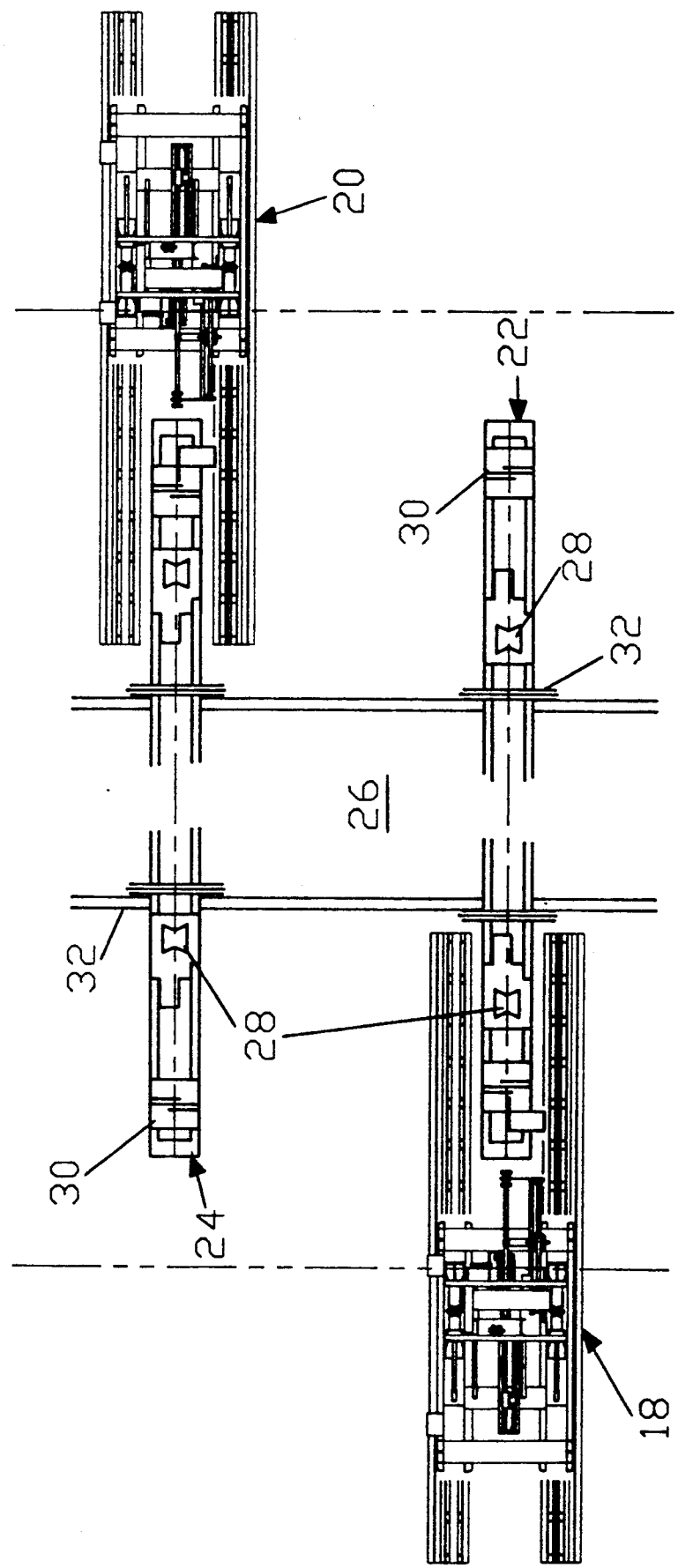
FIG. 4 is an overall plan view showing the apparatus and its placement with respect to the pipes being tested.

As shown in FIG. 4, the apparatus A comprises in two nearly identical stations 18 and 20, configured as shown in more detail in FIG. 1.

Ideally, station 18 is offset from station 20 so that one end of the pipe can be examined by station 18 and thereafter the opposite end is inspected by station 20. An alternative arrangement is possible where stations 18 and 20 are in alignment and simultaneously inspect both ends of the pipe. One disadvantage in doing this is that if there is a defect detected by one of the stations 18 or 20, the testing of the opposite end of the pipe would have been a wasted effort. By offsetting stations 18 and 20 and providing for interim storage in between, the possibility exists for lifting a pipe (not shown) off of rack 22 before it gets to rack 24. The production rate attainable is higher with an offset between stations 18 and 20 by allowing pipe storage between the two stations with a means (not shown) to remove the pipe from the assembly line if it is defective on the first end examined.

In the preferred embodiment, pipes to be tested are stored in a manner where they can be delivered to rack 22. After testing at station 18, means are provided in rack 22 to transfer the pipe to an intermediate storage area 26, and thereafter to rack 24. When located on racks 22 and 24, the pipe to be tested can be translated by a conveyor mechanism 28. The conveyor mechanism 28 can be a series of motor-driven pipe rolls or one motor-driven pipe roll with additional idler rolls. Once placed on racks 22 and 24, the pipe can be rotated about its longitudinal axis using rotator 30. The loader/unloader 32 is shown schematically for racks 22 and 24, and serves the purpose of bringing pipes onto and loading pipes off of racks 22 and 24 at the appropriate times. Having placed a pipe to be examined on rack 22, the conveyor mechanism 28 is actuated to assist in positioning the pipe for testing. The reason conveyor mechanism 28 is used is that there can be a great variety in length of even standard-sized lengths of pipe. For example, a standard 40-ft section of pipe can vary by as much as 10 feet. In that sense, the conveyor mechanism 28 serves as a coarse adjustment. The fine adjustment is done by manipulating base positioning means B as shown in FIG. 1. When doing so, frame 10 is moved until datum roll 34 (see FIG. 6) is brought into contact with a pipe 36 (FIG. 1). The pipe end or coupling, if provided, stays in contact with datum roll 34. Such contact is preferably maintained using base positioning means B, which exerts a predetermined force against pipe 36 through frame 10. Datum roll 34 rotates on its own axis to stay in contact with the pipe end or coupling as the pipe 36 is rotated on its own axis by rotator 30 (see FIG. 4). Conveyor mechanism 28 can move the pipe 36 into contact with datum roll 34.

Figure 5:
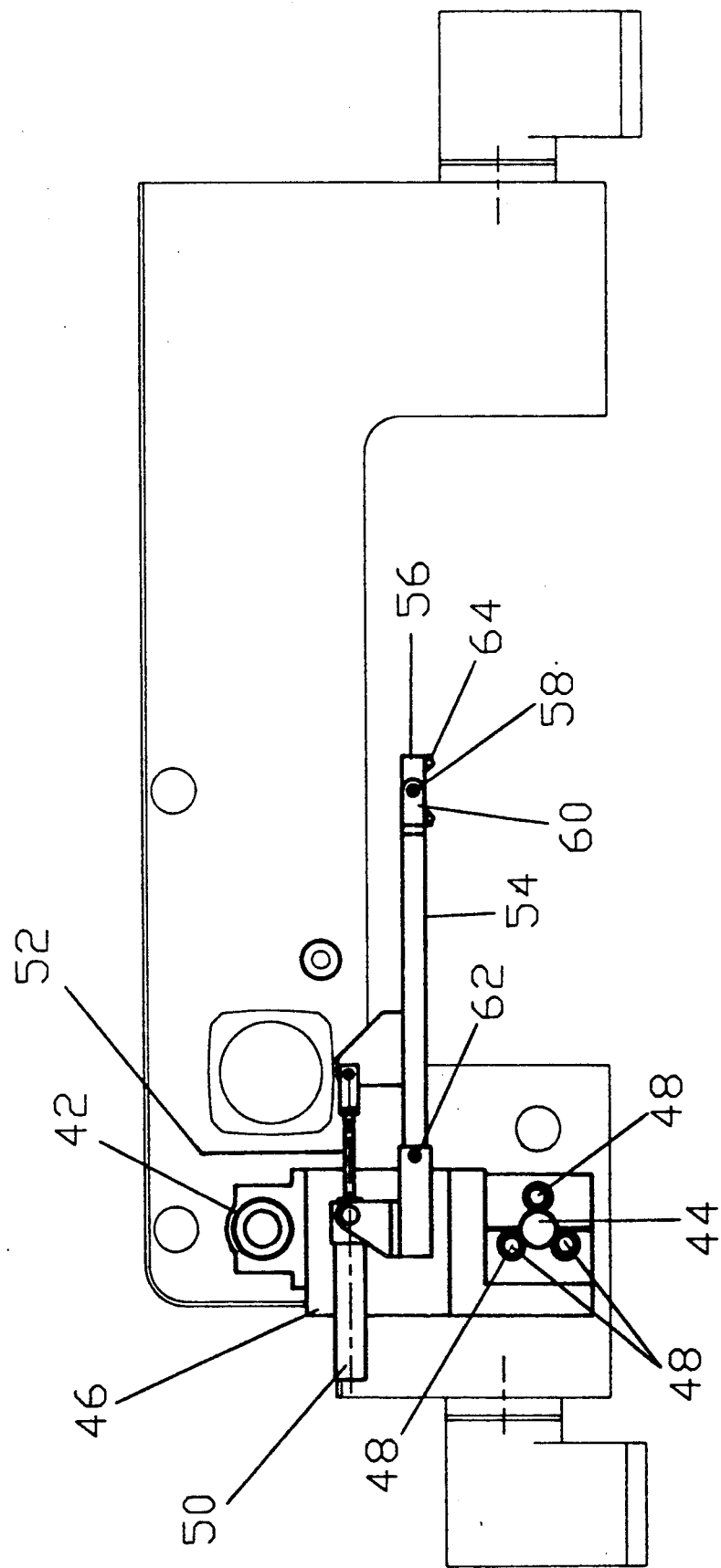
FIG. 5 is an elevational view of the outer surface sensor and support assembly.

When the pipe is brought into position, the outer surface inspection carriage and drive is tilted out of the way, as reflected in the dashed lines shown in FIG. 1. After the pipe is in position abutting datum roll 34, outer surface carriage support subframe 38 is swung down, as shown in the solid lines on FIG. 1. The outer surface carriage support subframe 38 has support rollers 40 that rest on the pipe 36 and support the outer surface carriage support subframe 38 as the pipe 36 rotates on its own axis. The outer surface carriage support subframe 38 is shown in details in FIGS. 1 and 5. As shown in FIG. 1, the outer surface carriage support subframe 38 has a guide shaft 42 and a drive shaft 44. A carriage 46 rides on shafts 42 and 44. As shown in FIG. 5, carriage 46 is driven along rotating shaft 44 by skewed bushings 48. Skewed bushings 48 are designed to apply a certain amount of force to carriage 46 to selectively drive it at a pre-selected speed. In the preferred embodiment, the carriage advances approximately $\frac{3}{8}$" per revolution of the pipe 36. The use of skewed bushings 48 further prevents damage to the components since resistance encountered by carriage 46 will cause bushings 48 to slip with respect to shaft 44. When this occurs, the carriage 46 simply stalls. Shaft 42 guides carriage 46.

Connected to carriage 46 is a power cylinder 50, which can be preferably pneumatically or hydraulically actuated to extend or retract shaft 52. Shaft 52 is connected to link 54, which is in turn connected to sensor mounting plate 56 at pivot 58. The eddy current sensor 60 is schematically shown in FIG. 5 as being connected to the underside of sensor mounting plate 56. Link 54 pivots with respect to point 62.

Actuation of cylinder 50 results in an arcuate movement of sensor 60 to selectively bring it in contact with a pipe 36. The additional pivot point 58 facilitates the placement of the sensor 60 adjacent the pipe outer surface. A pair of cushions 64 are provided to ride on the pipe surface and for accurate placement of sensor 60 with respect to the pipe outer surface. Cylinder 50 can also be used to regulate the amount of bearing force applied on sensor mounting plate 56 to maintain sensor 60 in proximity to the outer surface of the pipe 36. When pipe 36 is rotated on its own axis and skewed bushings 48 drive carriage 46, a helical pattern of movement is traced along the outside of the pipe 36 by sensor 60. It is within the scope of the invention to use multiple sensors disposed along pipe 36, each connected to cylinder 50 or through other corresponding cylinders and linkages, to provide a plurality of starting points for a plurality of sensors 60 so that multiple helical paths are traced on the outer surface of pipe 36 as it is rotated on its own axis. The carriage 46 can be placed so that the inspection begins at the end of the threads of a pipe 36 and continues toward the center of the pipe for a preferred distance of approximately 2 feet. Alternatively, the carriage 46 can be placed approximately 2 feet in from the end of a pipe 36, with the direction of motion of carriage 46 being in the reverse direction, toward the threads. The test is concluded in one pass. On return the speed of carriage 46 is increased to reduce the cycle time for the next pipe to be tested.

As shown in FIGS. 1, 2, and 3, the apparatus A of the present invention also provides for testing of the inner surface of the pipe and any internal thread provided on the end of the pipe 36 or on a coupling.

As shown in FIG. 1, a support subframe 66 supports a carriage 68. Carriage 68 is driven in the same manner as carriage 46. Rod 70 is connected to carriage 68. The sensor support assembly 72 is mounted to the opposite end of rod 70. The details of the sensor support assembly are shown in FIGS. 2 and 3. A hydraulic or preferably pneumatic cylinder 76 has a rod 78 extending therefrom and connected to link 80, which is in turn connected to pivotally mounted sensor support plate 82. The eddy current sensor 84 is mounted to plate 82. It should be noted that sensor support assembly 72 is capable of limited rotation about its longitudinal axis in the directions indicated by arrows 86, preferably a total range of travel of about 12 degrees. The linkage described above, in combination with the ability of sensor support assembly 72 to rotate about its longitudinal axis, allows sensor 84 to be specifically placed in contact with the inner surface of pipe 36 and allows it to respond to imperfections or out-of-roundness of the pipe 36. Cylinder 76 can be used to control the amount of applied pressure on sensor 84 when it contacts the inner surface of pipe 36. The use of multiple sensors 84 to track several helical paths is within the scope of the invention. For clarity, only one such assembly is illustrated.

Also located on sensor support assembly 72 is cylinder 88 (FIG. 3), which can be hydraulically or preferably pneumatically actuated. Cylinder 88 has a piston therein which is in turn connected to a shaft 90, which is in turn connected to a link 92, which is in turn connected to pivotally mounted sensor support plate 94, which in turn holds an eddy current sensor 96. The above described mechanism allows testing of inside threads using sensor 96. Cylinder 88 is separably actuated from cylinder 76. Sensor 96 can engage the inside thread or a coupling thread, and cylinder 88 can be used to maintain a certain contact pressure. Rotating of the pipe 36 on its own axis allows sensor 96 to ride the root of the thread. While this examination is going on, carriage 68 is pushed or pulled, depending on the direction of rotation of pipe 36, which in turn dictates the direction of travel of sensor 96 in the thread. The inner surface inspection can proceed in either direction by actuation of carriage 68, with sensor 84, into contact with the inner surface of the pipe 36 due to the operation of cylinder 76. At the conclusion of the pass by sensor 84, which traces a helical pattern due to the rotation of pipe 36. The sensor 84 is retracted from pipe 36 by cylinder 76, and cylinder 88 is actuated and sensor 96 is brought into contact with the inner surface of the pipe. The carriage 68 is then actuated to bring sensor 96 into the end of the thread at its root. Although a slight force longitudinally is continually applied by the carriage 68, the force of the pipe 36 spinning with sensor 96 in the root overcomes any pulling force exerted in the same direction and is the resultant driving force of the sensor 96. The threads may also be tested in the reverse direction. The inside threads may be tested at the same time as the inner surface by constructing sensor 96 with the ability to move longitudinally, independently of sensor 84.

Figure 6:
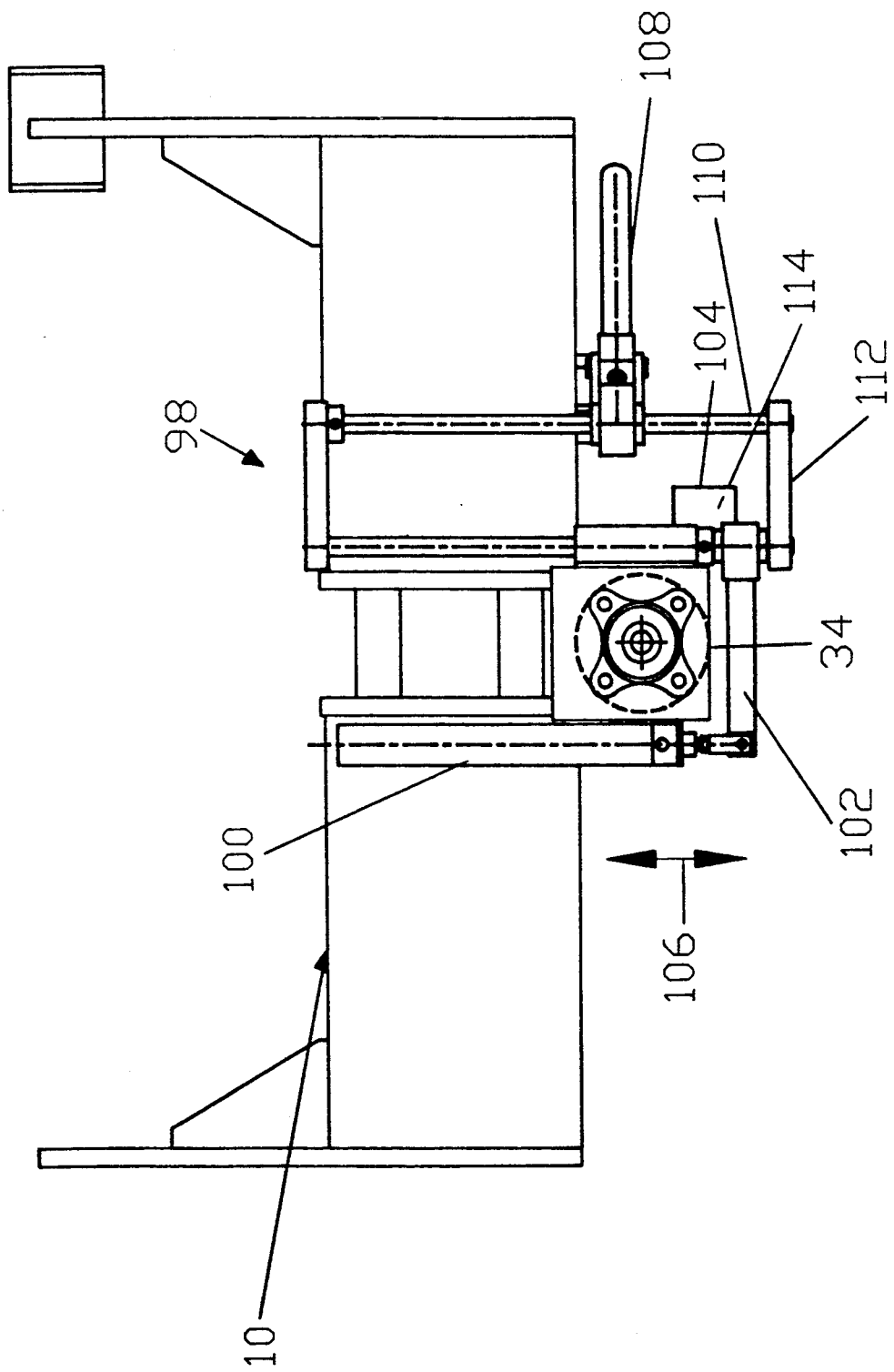
FIG. 6 is a plan view of the datum roll and the support mechanism for the external thread inspection sensor.

Similar principles are applicable to the thread-sensing feature for the external thread, as shown in FIGS. 1 and 6. The thread-sensing assembly is shown generally in FIG. 1 as number 98. As shown in FIG. 1, the outer thread-sensing assembly 98 is connected to frame 10. A cylinder 100 (FIG. 6) is connected to a link 102 for translation of the sensor support plate 104 in the direction shown by arrow 106. Another cylinder 108 displaces shaft 110, which in turn rotates link 112, which in turn rotates sensor support plate 104 into and out of contact with the outer surface of the pipe 36. A sensor 114 is located on the underside of sensor support plate 104.

In operation, the pipe 36 is butted up against datum roll 34. The thread testing can proceed before, after or during the outer surface testing. Cylinder 100 is actuated to selectively position sensor 114 at the start or the end of the thread. The inspection of the thread can proceed in either direction, depending upon the direction of rotation of pipe 36. For example, the testing can proceed from the end of the thread to the end of the pipe. If this occurs, the sensor 114 is moved in the direction away from the datum roll until it passes the end of the thread on pipe 36. Thereafter, cylinder 108 is actuated to put sensor 114 in contact with the outer surface of the pipe at a point slightly removed from the end of the thread. Cylinder 100 is then actuated to pull the sensor 114 toward the end of the thread. Cylinder 100 continues to apply a pulling force on the sensor after the sensor lands in the root of the thread. However, the force of the pipe 36 turning with sensor 114 in the root of the thread overcomes the pulling force exerted by cylinder 100. Cylinder 108 is used to maintain contact pressure of sensor 114 against the root of the thread on pipe 36. The testing can proceed in the reverse direction.

It should be noted that the outer surface test can be conducted simultaneously with the inner surface test and the thread test. If there is an internal thread, the internal thread test must be done separately from the inner surface test. However, a slightly different configuration providing independent support for sensors 84 and 96 are contemplated by the invention so that an internal thread test and an inner surface test can be conducted simultaneously. Various variables can be manipulated which affect the speed of testing. The rate of advance of the sensors 60 and 84 can be regulated. These two sensors take readings when making a pass in one direction. When these sensors travel in the opposite direction to return to their initial position, the rate of return can be dramatically increased to shorten the time it takes for the apparatus A to be ready to examine the next piece of pipe 36.

The contact pressure of the sensors described above against the pipe 36 can be regulated, as can the pulling force or pushing force exerted on these sensors during the testing by the various carriages and mechanisms to which they are connected. The apparatus A can be employed to test both ends of the same pipe at the same time by having two stations in line or, as shown in FIG. 4, the apparatus A can be in two opposing components offset from each other. This allows intermediate storage of pipe 36 therebetween, wherein one end of the pipe is tested and thereafter the other end is tested pending a successful result on the first test. Otherwise, the pipe section is removed from the assembly line.

Those skilled in the art can appreciate that only one station 18 can be employed and the pipe manipulated 180 degrees so that both ends can be tested.

One of the significant features of the invention is the slip feature in the carriage drives. In a situation where resistance to forward progress occurs to the particular sensor, the drive for the carriage involved stalls so that no damage occurs to the machine components. In the case of the thread sensor, cylinder 100 is regulated to apply a minimal thrust to the assembly supporting sensor 114 to the extent that such thrust is readily overcome by the turning pipe 36 pushing on the sensor 114, which, at that point is riding in the root of the thread.

The foregoing disclosure and description of the invention are illustrative and explanatory thereof, and various changes in the size, shape and materials, as well as in the details of the illustrated construction, may be made without departing from the spirit of the invention.

I claim:

1. A testing apparatus for a threaded pipe comprising a testing station, said testing station comprising
   a frame;
   a means for sensing faults on an outer surface of the pipe;
   means for sensing faults on an inner surface of an end of the pipe;
   means for sensing faults on thread located at an end of the pipe;
   a first, second, and third translation means connected, respectively, to said outer surface, said inner surface, and the thread fault sensing means and said frame to allow each of said sensing means independent movement to facilitate simultaneous sensing of the outer surface, inner surface, and thread of the pipe.

2. The apparatus of claim 1, further comprising:
   a first, second, and third positioning means connected, respectively, to said first, second, and third translation means for articulation of said outer surface, inner surface, and thread fault sensing means selectively into contact with the pipe.

3. A testing apparatus for a threaded pipe, comprising:
   a frame;
   means for sensing faults on an outer surface of the pipe;
   means for sensing faults on an inner surface of an end of the pipe;
   means for sensing faults on thread located at an end of the pipe;
   a first, second, and third positioning means connected, respectively, to said outer surface, said inner surface, and the thread fault sensing means and said frame to allow each of said sensing means independent movement to facilitate simultaneous sensing of the outer surface, inner surface, and thread of the pipe;
   a first, second and third positioning means connected, respectively, to said first, second, and third translation means for articulation of said outer surface, inner surface, and thread fault sensing means selectively into contact with the pipe; and
   said first, second, and third positioning means allow said sensor means to move in response to movement of the pipe while maintaining a pre-selected contact force with the pipe.

4. The apparatus of claim 3, further comprising:

support means for the pipe, said support means capable of translating the pipe and rotating it on its own axis;

indexing means on said frame for maintaining continuous contact with the pipe end as it is rotated on a central longitudinal axis thereof by said support means, said indexing means selectively moving said frame with respect to said support means to maintain said continuous contact.

5. The apparatus of claim 4, wherein said indexing means further comprises:

a roller mounted to said frame, an outer periphery of the roller maintaining continuous contact with the end of the pipe as it rotates;

a plurality of wheels mounted to said frame;

a track, said wheels moving on said track;

control means on said frame to selectively move said frame so that said roller contacts the pipe and maintains a pre-selected force on the pipe.

6. The apparatus of claim 5, wherein said first translation means further comprises:

a first subframe pivotally mounted to said frame to hold said outer surface-sensing means out of the way in a first position as the pipe is loaded onto said support means;

at least one idle roll engaging said pipe to provide support to said first subframe when it is selectively placed in a second position for outer surface testing;

a carriage movable on said first subframe;

first drive means on said first carriage to apply a pre-selected force to move said first carriage at a pre-selected speed, said drive means stalling said first carriage if a resistance force on said carriage exceeds the pre-selected driving force.

7. The apparatus of claim 6, wherein said second translation means comprises:

a second subframe connected to said frame;

a second carriage movable on said second subframe;

a second drive means on said second carriage to apply a pre-selected force to move said second carriage at a pre-selected speed, said drive means stalling if said second carriage encounters a resisting force which exceeds the pre-selected driving force;

said thread fault sensing means further comprising at least one inside thread sensor mounted to said second positioning means, whereupon selective operation of said second translation means and said second positioning means allows simultaneous or successive testing of the inner surface of the pipe and any internal thread.

8. The apparatus of claim 7, wherein said thread-sensing means further comprises:

at least one outer thread sensor;

said third translation means further comprises:

a first piston cylinder combination mounted to said frame for positioning said outer thread sensor at either end of an outside thread and to apply a pre-selected longitudinal force to said thread sensor when said thread-positioning means articulates said at least one outer thread sensor into a root of an external thread on the pipe;

said support means driving said at least one outer thread sensor along the root of said thread by virtue of rotation of the pipe on its longitudinal axis, whereupon the force exerted by said piston cylinder combination is overcome by said driving force from said support means.

9. The apparatus of claim 8, wherein said third translation means further comprises:

a third subframe movably mounted with respect to said frame;

said first piston cylinder combination extending said third subframe with said outer thread sensor, longitudinally, to locate said outer thread sensor on the root of the outside thread for initiating thread testing;

said third positioning means further comprises:

a second piston cylinder combination connected to said third subframe;

a linkage connecting said second piston cylinder combination to said outer thread sensor;

said second piston cylinder combination selectively moving said outer thread sensor into contact with the pipe and applying a pre-selected contact force.

10. The apparatus of claim 9 defining a testing station wherein said outer and inner surface-sensing means comprise a plurality of sensors with respect to the pipe, said outer and inner surface sensors respectively translated by said first and second translation means and articulated respectively by said first and second positioning means, whereby multiple helical paths are followed during testing of the outer and inner surfaces of the pipe;

all said sensors use an eddy current technique.

11. A testing apparatus for a threaded pipe, comprising:

a frame;

means for sensing faults on an outer surface of the pipe;

means for sensing faults on an inner surface of an end of the pipe;

means for sensing faults on thread located at an end of the pipe;

a first, second, and third translation means connected, respectively, to said outer surface, said inner surface, and the thread fault sensing means and said frame to allow each of said sensing means independent movement to facilitate simultaneous sensing of the outer surface, inner surface, and thread of the pipe; and said translation means holding said sensor means in a manner to allow their responsive movement to movements of the pipe while allowing said sensor means to maintain a pre-selected contact force with the pipe.

* * * * *